(12) United States Patent
Ukita et al.

(10) Patent No.: US 6,770,222 B1
(45) Date of Patent: Aug. 3, 2004

(54) POLYMERIZATION-INHIBITING COMPOSITION, POLYMERIZATION INHIBITOR AND METHOD FOR INHIBITING POLYMERIZATION

(75) Inventors: Keizo Ukita, Okayama (JP); Yuko Onodera, Okayama (JP)

(73) Assignee: Nippon Zeon Co., Ltd., Tokyo (JP)

( * ) Notice: Subject to any disclaimer, the term of this patent is extended or adjusted under 35 U.S.C. 154(b) by 0 days.

(21) Appl. No.: 09/623,377

(22) PCT Filed: Mar. 3, 1999

(86) PCT No.: PCT/JP99/01017

§ 371 (c)(1),
(2), (4) Date: Sep. 1, 2000

(87) PCT Pub. No.: WO99/44972

PCT Pub. Date: Sep. 10, 1999

(30) Foreign Application Priority Data

Mar. 3, 1998 (JP) .......................................... 10-067872
Sep. 30, 1998 (JP) .......................................... 10-292987

(51) Int. Cl.[7] .............................................. C08K 5/06
(52) U.S. Cl. ..................... 252/399; 252/394; 252/398; 252/400
(58) Field of Search ................................ 252/399, 394, 252/398, 400

(56) References Cited

U.S. PATENT DOCUMENTS 3,371,124 A    2/1968  Albert et al.
3,818,079 A  * 6/1974  Sato et al.
4,127,603 A  * 11/1978 Bljumberg et al. ......... 562/533
5,155,148 A  * 10/1992 Parker et al. ................. 524/83
5,504,243 A  *  4/1996 Sakamoto et al. .......... 560/205
5,856,562 A  *  1/1999 Mine et al. .................. 560/205

FOREIGN PATENT DOCUMENTS

| JP | 41-17458 | 10/1964 |
| JP | 47-41323 | 10/1972 |
| JP | 50-112304 | 9/1975 |
| JP | 60-237065 | 11/1985 |
| JP | 4-26639 | 5/1992 |
| JP | 4-189810 | 7/1992 |
| JP | 4-233905 | 8/1992 |
| JP | 4-233906 | 8/1992 |
| JP | 4-233907 | 8/1992 |
| JP | 4-288302 | 10/1992 |
| JP | 5-202256 | 8/1993 |
| JP | 9-316026 | 12/1997 |

* cited by examiner

*Primary Examiner*—Margaret B. Medley
(74) *Attorney, Agent, or Firm*—Dinsmore & Shohl LLP (57) ABSTRACT

The invention relates to a polymerization inhibitor comprising at least one compound (a) selected from the group consisting of a compound having an NO radical in its molecule and a precursor compound capable of forming an NO radical, and a phosphorus-containing compound (b), wherein a weight ratio of the compound (a) to the phosphorus-containing compound (b) is 1:10 to 100:1.

Specifically, the invention provides a method for inhibiting the polymerization of at least one monomer (c) selected from the group consisting of a conjugated diene, an aromatic vinyl, an ethylenically unsaturated nitrile and an α-olefin, comprising causing the polymerization inhibitor to coexist with the monomer (c), and a polymerization-inhibiting composition comprising the polymerization inhibitor and the monomer (c).

21 Claims, 1 Drawing Sheet

FIG. 1

POLYMERIZATION-INHIBITING COMPOSITION, POLYMERIZATION INHIBITOR AND METHOD FOR INHIBITING POLYMERIZATION

TECHNICAL FIELD

The present invention relates to techniques for inhibiting the polymerization of a monomer such as a conjugated diene, aromatic vinyl, ethylenically unsaturated nitrile or α-olefin, and more particularly to a polymerization-inhibiting composition, a polymerization inhibitor and a polymerization-inhibiting method for inhibiting the occurrence of unfavorable premature polymerization in various operating steps such as the production, purification, storage, shipment, preparation and use of such a monomer, a mixture of the monomers or a hydrocarbon mixture containing the monomer.

BACKGROUND ART

A monomer such as a conjugated diene, aromatic vinyl, ethylenically unsaturated nitrile or α-olefin is easy to cause premature polymerization in various operating steps such as the production, purification, storage, shipment, preparation and use thereof. The occurrence of the premature polymerization causes contamination of the monomer with a polymer, increase of viscosity, gelling, loss in reactivity, etc. In addition, by the premature polymerization, a heat exchanger, storage container, transfer line, pump, distilling apparatus or the like is stained with the polymer, and so problems such as increase in the cost of washing, lowering in production efficiency and loss of material occur. The problems relating to such premature polymerization will be described more specifically taking the case of a purification step of a conjugated diene.

Conjugated dienes, conjugated diene-containing hydrocarbon mixtures (for example, $C_4$ hydrocarbon fraction and $C_5$ hydrocarbon fraction), conjugated diene-containing unsaturated olefin hydrocarbon mixtures (mixtures in a recovery step of olefin hydrocarbon compounds after gas and liquid cracking or decomposing processes), conjugated diene-containing monomer mixtures (for example, monomer mixtures for production of synthetic rubbers) and the like are easy to undergo polymerization of the conjugated dienes and/or copolymerization of the conjugated dienes with any other copolymerizable unsaturated compound upon distillation, extractive distillation, extraction, countercurrent extraction, hydrogenation or hydrotreating, hydrorefining, heat treatment, other similar treatments, preheating before treatment, storage, transfer or processing.

For example, when a purified conjugated diene is isolated and recovered from a conjugated diene-containing hydrocarbon mixture by a distillation process including extractive distillation, a polymerization reaction is easy to occur to form a solvent-soluble polymer or a crosslinked, solvent-insoluble polymer. The solvent-soluble polymer is called a rubbery polymer and stains various apparatus or devices such as an extractive distillation column, distillation column, heat exchanger and piping. The crosslinked, solvent-insoluble polymer is a porous insoluble polymer and is called a popcorn polymer due to its appearance. This popcorn polymer is particularly undesirable because not only it self-multiplies in the presence of the vapor or liquid of the conjugated diene to rapidly clog the apparatus, but it is extremely difficult to remove and control. Once the popcorn polymer is formed, it multiplies, so to speak, exponentially, in that it serves as a seed. Since the popcorn polymer is a strong crosslinked polymer, it is insoluble in any already-known solvent and not melted. Accordingly, in order to remove the popcorn polymer, there is no effective cleaning method, but it is cleaned out by a mechanical means. The cleaning of the apparatus requires to suspend and disjoint it so as to mechanically remove the deposit of the polymer, and so it takes time, and economical disadvantage is unavoidable. In addition, since the popcorn polymer cannot be completely removed by the mechanical cleaning, the popcorn polymer remaining in the apparatus in a trace amount serves as a seed to start the multiplication of the popcorn polymer again when the operation of the apparatus is resumed.

In a process of preparing a purified conjugated diene by subjecting a hydrocarbon mixture containing the conjugated diene to a distillation process including extractive distillation, conditions liable to induce a polymerization reaction, such as coexistence of a gas phase with a liquid phase, moderate operating temperature, high monomer purity, mixing of water and presence of iron rust, gather. Accordingly, there have heretofore been proposed methods making use of various kinds of polymerization inhibitors. However, in some cases, the insufficient polymerization inhibiting effects thereof may have made it difficult to prevent the formation of a rubbery polymer and/or a popcorn polymer, so that the apparatus is clogged. When the polymerization inhibitor is used in a large amount to enhance the polymerization inhibiting effect, there occur such problems that a tar-like product is formed to waste energy, and the extraction efficiency of the extractive distillation is lowered.

In a process of recovering an olefin hydrocarbon compound such as ethylene, propylene, butene, butadiene or a mixture thereof after gas and liquid cracking or decomposing processes, treatments such as an isolating process of various kinds of olefin hydrocarbon compounds are conducted by conversion by hydrogenation, distillation or extraction of olefin compounds and acetylene compounds. Deposit (scale) considered to be attributable to the polymerization of conjugated dienes and/or the like is easy to form on apparatus for these treatments. When such deposit is built up to an excessive extent, thermal efficiency of the apparatus and isolation efficiency of a distillation column are lowered, and clogging of piping is caused. In addition, a monomer mixture containing a conjugated diene and a vinyl aromatic compound such as styrene has been known to show a tendency to polymerize during its storage.

There has heretofore been proposed a method of distilling a $C_5$ hydrocarbon fraction in the presence of N,N-dialkylhydroxylamine in order to inhibit the polymerization of a conjugated diene-containing petroleum fraction in a distillation apparatus (Japanese Patent Application Laid-Open No. 112304/1975). However, the mere use of N,N-dialkylhydroxylamine is not sufficient in the polymerization-inhibiting effect. U.S. Pat. No. 3,371,124 has proposed a method of using N,N-dialkyl-hydroxylamine and the oxalate [bis(diethylhydroxylamine) oxalate] thereof as polymerization inhibitors in order to inhibit the formation of a popcorn polymer in a recovery system by fractional distillation of a monomer containing at least one conjugated diene discharged from a production process of SBR. The oxalate can be obtained by reacting N,N-dialkylhydroxylamine with oxalic acid. However, oxalic acid involves a problem that it corrodes an extractive distillation column. The mere use of the oxalate is not sufficient in the polymerization-inhibiting effect.

Japanese Patent Application Laid-Open No. 189810/1992 discloses a method of causing [Group A] hydroquinone, hydroquinone monomethyl ether, p-methoxyphenyl, phenothiazine, piperidine, etc. and [Group B] phosphorus-containing compounds such as phosphoric acid and potassium phosphate to coexist with a molecular oxygen-containing gas in order to inhibit thermal polymerization upon epoxidation of a double bond in a cyclohexenyl ring by causing an epoxidizing agent to act on a mixture of (meth) acrylates having a cyclohexenyl group in their ester moieties. However, it has been found that when a combination of hydroquinone shown as a representative example of Group A in this publication with a phosphorus-containing compound in Group B is used to conduct extractive distillation of a conjugated diene-containing hydrocarbon mixture, a sufficient polymerization-inhibiting effect cannot be achieved.

Further, it has heretofore been proposed to use a compound having a stable NO radical (free radical) in its molecule or a compound forming a stable NO radical in situ under treating conditions as a polymerization inhibitor (Japanese Patent Publication No. 26639/1992, etc.). However, the mere use of these compounds fails to achieve a sufficient polymerization-inhibiting effect.

Such problems of premature polymerization are easy to occur at various operating steps in not only conjugated dienes, but also many other monomers.

DISCLOSURE OF THE INVENTION

It is an object of the present invention to provide a polymerization inhibitor and a method of inhibiting polymerization for inhibiting the occurrence of unfavorable premature polymerization in various operating steps such as the production, purification, storage, shipment, preparation and use of a monomer such as a conjugated diene, aromatic vinyl, ethylenically unsaturated nitrile or α-olefin, a mixture of the monomers or a hydrocarbon mixture containing such a monomer.

Another object of the present invention is to provide a polymerization-inhibiting composition containing the monomer and polymerization inhibitor described above.

A particular object of the present invention is to provide a novel polymerization inhibitor, method of inhibiting polymerization and polymerization-inhibiting composition containing a conjugated diene and the polymerization inhibitor for inhibiting (co)polymerization of the conjugated diene upon the treatment, storage or the like of the conjugated diene, a conjugated diene-containing hydrocarbon mixture, a conjugated diene-containing unsaturated olefin hydrocarbon mixture, a conjugated diene-containing monomer mixture, or the like at a high level.

The present inventors have carried out an extensive investigation with a view toward overcoming the above-described problems involved in the prior art. As a result, it has been found that the combined use of at least one compound selected from the group consisting of a compound having an NO radical (NO) in its molecule and a precursor compound capable of forming an NO radical and a phosphorus-containing compound as a polymerization inhibitor is extremely effective for the inhibition of premature polymerization of various kinds of monomers such as conjugated dienes.

The polymerization inhibitor according to the present invention can markedly inhibit the formation of a popcorn polymer and a rubbery polymer when it is caused to exist in a distillation step in a process for isolating and producing a purified conjugated diene by conducting a distillation process including extractive distillation from, for example, a conjugated diene-containing hydrocarbon mixture. The polymerization inhibitor according to the present invention is extremely effective for not only hydrocarbon mixtures and the like containing a conjugated diene in a great amount, but also hydrocarbon mixtures and the like containing a conjugated diene in a small amount. The polymerization inhibitor according to the present invention is also effective for the inhibition of polymerization of monomers such as aromatic vinyls, ethylenically unsaturated nitrites and α-olefins. The present invention has been led to completion on the basis of these findings.

According to the present invention, there is thus provided a polymerization-inhibiting composition comprising at least one compound (a) selected from the group consisting of a compound having an NO radical in its molecule and a precursor compound capable of forming an NO radical, a phosphorus-containing compound (b), and at least one monomer (c) selected from the group consisting of a conjugated diene, an aromatic vinyl, an ethylenically unsaturated nitrile and an α-olefin, wherein a weight ratio of the compound (a) to the phosphorus-containing compound (b) is 1:10 to 100:1.

According to the present invention, there is also provided a polymerization inhibitor for at least one monomer (c) selected from the group consisting of a conjugated diene, an aromatic vinyl, an ethylenically unsaturated nitrile and an α-olefin, comprising at least one compound (a) selected from the group consisting of a compound having an NO radical in its molecule and a precursor compound capable of forming an NO radical, and a phosphorus-containing compound (b), wherein a weight ratio of the compound (a) to the phosphorus-containing compound (b) is 1:10 to 100:1.

According to the present invention, there is further provided a method for inhibiting polymerization, which comprises causing at least one compound (a) selected from the group consisting of a compound having an NO radical in its molecule and a precursor compound capable of forming an NO radical, and a phosphorus-containing compound (b) to coexist at a weight ratio of the compound (a) to the phosphorus-containing compound (b) of 1:10 to 100:1 with at least one monomer (c) selected from the group consisting of a conjugated diene, an aromatic vinyl, an ethylenically unsaturated nitrile and an α-olefin.

BEST MODE FOR CARRYING OUT THE INVENTION

1. Monomer

The polymerization-inhibiting technique according to the present invention can be applied to conjugated dienes, aromatic vinyls, ethylenically unsaturated nitrites and α-olefins. Examples of the conjugated dienes include 1,3-butadiene, isoprene, chloroprene and the like. Examples of the aromatic vinyls include styrene, vinyltoluene, α-methylstyrene and the like. Examples of the ethylenically unsaturated nitriles include acrylonitrile, methacrylonitrile and the like. Examples of the α-olefins include ethylene, propylene, 1-butene, 1-pentene, 1-hexene, 1-heptene, 1-octene and the like.

Among others, the polymerization inhibitor according to the present invention is particularly effective for inhibiting the formation of a popcorn polymer and a rubbery polymer in a production process of a purified conjugated diene, comprising isolating the conjugated diene by conducting a distillation process including extractive distillation from a conjugated diene-containing hydrocarbon mixture. The conjugated dienes will hereinafter be described in detail.

2. Conjugated Diene

In the present invention, as the conjugated dienes, may be mentioned 1,3-butadiene, isoprene, chloroprene and the like. The polymerization inhibitor according to the present invention is suitable for conjugated dienes or conjugated diene-containing mixtures. As the conjugated diene-containing mixtures, may be mentioned conjugated diene-containing hydrocarbon mixtures, conjugated diene-containing unsaturated olefin hydrocarbon mixtures, conjugated diene-containing monomer mixtures and the like.

The conjugated diene-containing hydrocarbon mixture is a mixture of various kinds of hydrocarbons containing at least one conjugated diene. No particular limitation is imposed on a conjugated diene-containing hydrocarbon mixture used as a starting material for isolating and producing a purified conjugated diene. However, as representative examples thereof, may be mentioned petroleum fractions such as an isoprene-containing $C_5$ hydrocarbon fraction and a 1,3-butadiene-containing $C_4$ hydrocarbon fraction.

The $C_5$ hydrocarbon fraction is secondarily produced upon the production of ethylene by steam cracking or another high-temperature treatment of a hydrocarbon. The $C_5$ hydrocarbon fraction generally has a boiling point ranging from 25° C. to 70° C. and contains various kinds of $C_5$ hydrocarbons different in degree of saturation and may contain some $C_4$ hydrocarbons and $C_6$ hydrocarbons. The $C_5$ hydrocarbon fraction generally contains n-pentane, isopentane, 1-pentene, 2-methyl-1-butene, trans-2-pentene, cis-2-pentene, 2-methyl-2-butene, isoprene, trans-1,3-pentadiene, cis-1,3-pentadiene, 1,4-pentadiene, 2-butyne, isopropenylacetylene, isopropylacetylene, cyclopentane, cyclopentene, cyclopentadiene and the like.

The $C_4$ hydrocarbon fraction such as naphtha-cracked oil generally contains various kinds of hydrocarbons such as propane, propylene, isobutene, allene, n-butane, isobutene, 1-butene, trans-2-butene, cis-2-butene, 1,3-butadiene, methylacetylene, 1,2-butadiene and vinylacetylene.

As the conjugated diene-containing unsaturated olefin hydrocarbon mixtures, may be mentioned unsaturated olefin hydrocarbon mixtures in a recovery step of olefin hydrocarbon compounds such as ethylene, propylene, butene, butadiene and mixtures thereof after gas and liquid cracking or decomposing processes. Ethylene, propylene, butene, butadiene and the like are isolated and recovered from these unsaturated olefin hydrocarbon mixtures by a process including hydrogenation, distillation, extraction and/or the like.

As examples of the conjugated diene-containing monomer mixtures, may be mentioned monomer mixtures for preparation of synthetic rubber such as SBR.

The polymerization inhibitor according to the present invention can be applied to conjugated diene-containing liquid mixtures in addition to the above-described mixtures.

3. Extractive Distillation

The polymerization inhibitor according to the present invention is particularly suitable for use in inhibiting the formation of a popcorn polymer and a rubbery polymer in an extractive distillation step in a process for isolating and producing a purified conjugated diene by conducting a distillation process including extractive distillation from a conjugated diene-containing hydrocarbon mixture. Therefore, the extractive distillation will hereinafter be described in detail.

As the distillation process including extractive distillation, a single extractive distillation process or a combination of plural extractive distillation processes may be only conducted. However, when a hydrocarbon mixture containing many kinds of hydrocarbons is used as a starting material, an extractive distillation step may also be combined with a distillation step (fractional distillation step) making good use of a difference between boiling points.

As an example of the distillation process including extractive distillation, may be mentioned a process for recovering high-purity isoprene from a $C_5$ hydrocarbon mixture described in Japanese Patent Publication No. 41323/1972. More specifically, this publication describes a process for recovering high-purity isoprene, in which (1) a $C_5$ hydrocarbon mixture as a raw material is subjected to extractive distillation in the presence of an N-alkyl-substituted lower fatty acid amide solvent containing a polymerization inhibitor to remove hydrocarbons more hardly soluble than isoprene, (2) the thus-extracted isoprene and hydrocarbons more easily soluble than isoprene are then distilled to remove most of cyclopentadiene and hydrocarbons having a higher boiling point than isoprene, (3) the resultant fraction is subjected further to extractive distillation in the presence of the above-described solvent to remove the remaining cyclopentadiene and easily soluble hydrocarbons such as isopropenylacetylene, and (4) the solvent before circulating to the extractive distillation is subjected to a stripping treatment under such reduced pressure that the stripping temperature amounts to 140° C. or lower. In the publication, a flow diagram of the recovery process is illustrated and quoted for reference in explanation of the present invention.

Figure 1:
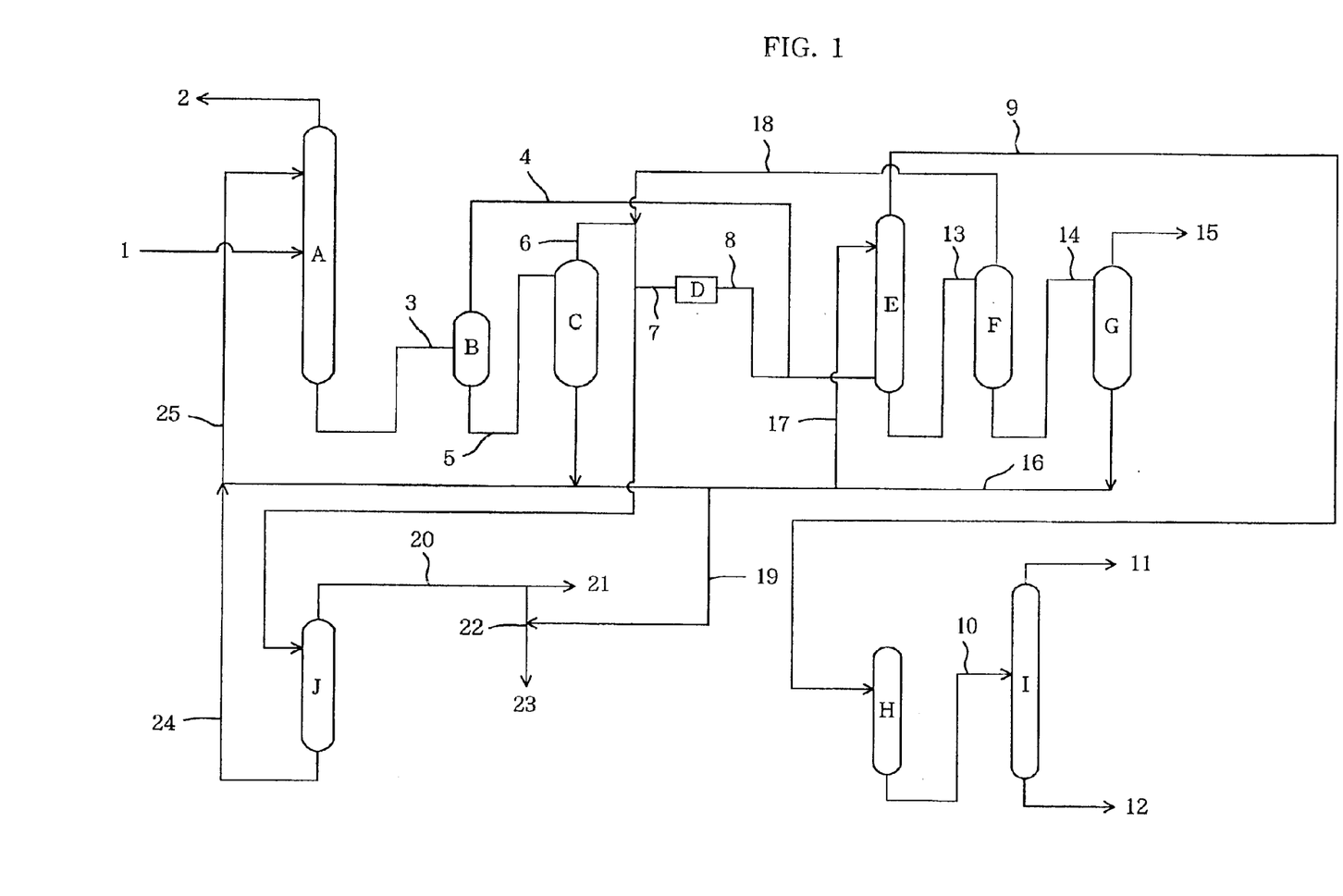
FIG. 1 is a flow diagram illustrating a distillation process including an extractive distillation step for obtaining purified 1,3-butadiene from a $C_4$ hydrocarbon fraction.

As an example of a process for preparing (recovering) purified 1,3-butadiene by a distillation process including extractive distillation from a $C_4$ hydrocarbon fraction containing 1,3-butadiene, may be mentioned a process illustrated in FIG. 1. However, for example, reboilers, condensers, heat exchangers, coolers, pumps, circulating circuits in respective distillation columns, and the like are omitted in FIG. 1 for the sake of brief description of the whole distillation process.

As illustrated in FIG. 1, a gasified $C_4$ hydrocarbon fraction is fed to a middle stage of a first extractive distillation column A through a pipe 21, while an extraction solvent such as N,N-dimethylformamide is fed thereto through a pipe 45 to conduct first-stage extractive distillation. In the first-stage extractive distillation, a raffinate composed of hydrocarbons (propane, propylene, isobutene, allene, n-butane, isobutene, 1-butene, trans-2-butene, cis-2-butene, etc.) lower in solubility in the extraction solvent than 1,3-butadiene is removed from the top of the column through a pipe 22. The main component of the raffinate is butene. However, the gas discharged from the top of the column is condensed by a condenser though not illustrated, and a part of the condensate is returned to the top of the column by refluxing. The pressure within the first distillation column is generally 1 to 15 atm, and the temperature at the bottom of the column is generally 100 to 180° C. The number of plates in the extractive distillation column may be suitably preset and is generally 100 to 300 plates and often about 200 plates in the case where the $C_4$ hydrocarbon fraction is used.

An extract containing 1,3-butadiene and hydrocarbons (methylacetylene, 1,2-butadiene, vinylacetylene, etc.) higher in solubility in the extraction solvent than 1,3-butadiene is taken out of the bottom of the first distillation column A and fed to an upper part of a preliminary stripping column B through a pipe 23. In the preliminary stripping column B, the hydrocarbons are partially stripped from the solvent and directly sent to a second distillation column E through a pipe 24. The bottoms in the preliminary stripping column B are fed to the top of a first stripping column C through a pipe 25, and the hydrocarbons are stripped from the solvent. The solvent discharged from the bottom of the first stripping column is cooled in a heat exchanger and circulated into the first extractive distillation column A. A hydrocarbon vapor discharged from the top of the first stripping column is introduced into a compressor D through pipes 26 and 27, compressed there and then fed to the bottom of a second extractive distillation column E through a pipe 28. The preliminary stripping column B and first stripping column C can be operated under conditions that the pressure within each column is generally 1 to 2 atm, and the temperature at the bottom thereof is the boiling point of the solvent at the pressure thereof.

1,3-Butadiene and hydrocarbons higher in solubility in the extraction solvent than 1,3-butadiene are mainly fed to the second extractive distillation column E. An extraction solvent is fed to a position lower by some plates than the top of the second extractive distillation column E through a pipe 37. A vapor discharged from the top of the second extractive distillation column is 1,3-butadiene containing a trace amount of impurities and refluxed by a condenser, and the remaining portion thereof is sent to a first fractional distillation column H through a pipe 29. A liquid composed mainly of the solvent at the bottom of the second extractive distillation column E is first fed to a butadiene recovering column F through a pipe 33 and then to a second stripping column G through a pipe 34, and the remaining hydrocarbons are stripped from the solvent there. The solvent discharged from the bottom of the second stripping column G is cooled by heat exchange and returned to the first extractive distillation column A and second extractive distillation column E through a pipe 36. A vapor at the top of the second stripping column G is refluxed by a condenser, and a gas remaining without being refluxed is discharged into a fuel gas system through a pipe 35. The operating conditions of the second extractive distillation column and second stripping column are the same as those of the first extractive distillation column and first stripping column, respectively.

Since a small amount of impurities still remain in a 1,3-butadiene fraction even by the two-stage extractive distillation, these impurities are removed by fractional distillation. In the first fractional distillation column H, impurities having a boiling point lower than that of 1,3-butadiene are removed. A vapor at the top of the first fractional distillation column H is partially condensed and refluxed, and the remainder is sent to the fuel gas system. The bottoms in the first fractional distillation column H are sent to a second fractional distillation column I though a pipe 30. A distillate from the second fractional distillation column I is provided as a 1,3-butadiene product through a pipe 31. The bottoms in the second fractional distillation column I are discharged as a waste liquid. The operating conditions of the respective fractional distillation columns are such that the pressure within each column is generally 1 to 15 atm, and the temperature within the column is the boiling point of the intended product at the pressure thereof. The number of plates in each distillation column may be suitably preset and is generally 50 to 200 plates and often about 100 plates in the case where the $C_4$ hydrocarbon fraction is used.

The extraction solvent is sent to a solvent-purifying column J, and the solvent purified by washing with water is returned to the extractive distillation columns though a pipe 44. Water and a waste liquid are discharged through a pipe 40 and out of a pipe 41 for water and out of a pipe 43 for the waste liquid.

In order to isolating and recovering a conjugated diene from the $C_5$ hydrocarbon fraction and $C_4$ hydrocarbon fraction, as described above, there is adopted a distillation process in which ① a two-stage extractive distillation step with the object of removing hardly soluble hydrocarbons and easily soluble hydrocarbons and ② a fractional distillation step of generally two stages making good use of a difference between boiling points, which is conducted between the extractive distillation steps of two stages or as a final step, are suitably combined with each other.

As the extraction solvent, is used any of various solvents which can dissolve and extract conjugated dienes and generally used in a technical field relating to extractive distillation, such as amide compounds, N-methylpyrrolidone, acetonitrile and N-formylmorpholine. Among these extraction solvents, amide compounds are preferred. As examples of the amide compounds, may be mentioned formamide, N,N-dimethylformamide, acetamide, N-ethylacetamide, N,N-dimethylacetamide, N-chloroacetamide, N-bromoacetamide, diacetamide, triacetamide, propionamide, butylamide, isobutylamide, valeramide, isovaleramide, hexanamide, heptanamide, octanamide, decanamide, acrylamide, chloroacetamide, dichloroacetamide, trichloroacetamide, glycol amide, lactamide, pyruvoamide, cyanoacetamide, 2-cyano-2-nitroacetamide, oxamide, malonamide, succinamide, adipamide, malamide, d-tartramide and N,N-dimethylacetoacetic acid amide. Among these, N,N-dimethylformamide (DMF) is particularly preferred.

Examples of extraction solvents other than those described above include acetone, methyl ethyl ketone, dioxane, isoprene cyclic sulfone, acetonitrile, alcohol, glycol, N-methylolamine, N-ethylsuccinimide, N-methylpyrrolidone, hydroxyethylpyrrolidone, N-methyl-5-methylpyrrolidone, 2-heptenone, morpholine, N-formylmorpholine, N-methylmorpholin-3-on, sulfolane, methylcarbitol, tetrahydrofuran, aniline, N-methyloxazolidone, N-methyl-imidazole, N,N'-dimethylimidazolin-2-on, methyl cyanoacetate, ethyl acetoacetate, ethyl acetate, dimethyl malonate, propylene carbonate, methylcarbitol, diethylene glycol monomethyl ether, dimethyl sulfoxide and γ-butyrolactone.

A proportion of the extraction solvent used is generally 100 to 1,000 parts by weight, preferably 200 to 800 parts by weight per 100 parts by weight of the conjugated diene-containing hydrocarbon mixture. The extraction solvent is fed into each extractive distillation column from a position higher than a position in the column to which the hydrocarbon mixture is fed.

4. Polymerization Inhibitor

In the present invention, a polymerization inhibitor composed of a combination of at least one compound (a) selected from the group consisting of a compound having an NO radical in its molecule and a precursor compound capable of forming an NO radical, and a phosphorus-containing compound (b) is used as a polymerization inhibitor for conjugated dienes.

Compound (a)

The compound (a) includes inorganic compounds and organic compounds. As specific examples thereof, may be mentioned the following various compounds:

(1) N,N-Dialkylhydroxylamines represented by the formula (I):

wherein $R_1$ and $R_2$ are independently a linear, branched or cyclic alkyl group having 1 to 10 carbon atoms.

The number of carbon atoms in the alkyl group is preferably 1 to 6. Examples of the alkyl group include methyl, ethyl, propyl, isopropyl, butyl, pentyl and cyclohexyl groups. The N,N-dialkylhydroxylamine is preferably N,N-diethylhydroxylamine (DEHA).

(2) Such nitroxyl compounds (compounds having an NO radical in their molecules) of sterically hindered amines as disclosed in Japanese Patent Publication No. 237065/1985.

The nitroxyl compound (also referred to as N-oxyl or nitroxide) is a free radical having an unpaired electron and represented by the following formula (II):

wherein the nitrogen atom is bonded directly to 2 tetrasubstituted carbon atoms, $E_1$, $E_2$, $E_3$ and $E_4$ are independently an organic group, and T is an organic group required to form a 5- or 6-membered ring.

$E_1$, $E_2$, $E_3$ and $E_4$ are preferably methyl groups. As examples of the nitroxyl compounds, may be mentioned 4-hydroxy-2,2,6,6-tetramethylpiperidine-1-oxyl, 4-oxo-2,2,6,6-tetramethylpiperidine-1-oxyl, 4-benzoyloxy-2,2,6,6-tetramethylpiperidine-1-oxyl, 3-carbamoyl-2,2,5,5-tetramethylpyrrolidine-1-oxyl, N-(1-oxyl-2,2,6,6-tetramethylpiperidin-4-yl-ε-caprolactam, 3-oxyl-2,2,4,4-tetramethyl-7-oxa-3,20-diazaspiro[5.1.11.2]heneicosan-21-on, 4-aza-3,3-dimethyl-4-oxyl-1-oxaspiro[4.5]decane and 2,4,4-trimethyl-2-phenyloxazolidine-3-oxyl.

(3) Hydroxylamine compounds corresponding to such nitroxyl compounds of sterically hindered amines as disclosed in Japanese Patent Application Laid-Open No. 237065/1985.

The hydroxylamine compound is a precursor compound capable of forming an NO radical (free radical) in situ in a system to which the polymerization inhibitor has been added and represented by the following formula (III):

wherein the nitrogen atom is bonded directly to 2 tetrasubstituted carbon atoms, $E_1$, $E_2$, $E_3$ and $E_4$ are independently an organic group, and T is an organic group required to form a 5- or 6-membered ring.

$E_1$, $E_2$, $E_3$ and $E_4$ are preferably methyl groups. As examples of the hydroxylamine compounds, may be mentioned 1,4-dihydroxy-2,2,6,6-tetramethylpiperidine, 4-benzoyloxy-1-hydroxy-2,2,6,6-tetramethylpiperidine, di(1-hydroxy-2,2,6,6-tetramethylpiperidin-4-yl) sebacate and N-(1-hydroxy-2,2,6,6-tetramethylpiperidin-4-yl)-ε-caprolactam.

(4) Such nitrogen oxides having a stable free radical, precursor compounds capable of forming a stable free radical in situ, etc. as disclosed in Japanese Patent Publication No. 26639/1992.

Examples of the nitrogen oxides having a stable free radical (free radical existing for such a long period of time as being detectable in a static system by an ordinary spectroscopic method; half-life: generally at least 1 year) include di-t-butylnitroxide, piperidinyl-1-oxy compounds, pyrrolidine-1-oxy compounds and pyrroline-1-oxy compounds. Examples of the piperidinyl-1-oxy compounds include 4-hydroxy-2,2,6,6-tetramethylpiperidino-1-oxy, 4-oxo-2,2,6,6-tetramethylpiperidino-1-oxy and 2,2,6,6-tetramethylpiperidino-1-oxy.

Examples of the precursor compounds capable of forming a stable free radical in situ include nitrones, nitrosos, thioketones, benzoquinones and hydroxylamines. Nitrosophenylhydroxylamines and the ammonium salts thereof may also be mentioned.

(5) Reaction products of an N,N-di-lower alkylhydroxylamine with an organic acid disclosed in U.S. Pat. No. 3,371,124 and Japanese Patent Publication No. 17458/1966.

As examples of such reaction products, may be mentioned the above-described oxalates [bis(diethyl-hydroxylamine) oxalate] of N,N-dialkylhydroxylamines and the N,N-di-lower alkylhydroxylamine salts of oxyacids or polycarboxylic acids described in Japanese Patent Publication No. 17458/1966.

The lower alkyl groups in the N,N-di-lower alkylhydroxylamines include methyl, ethyl, propyl, isopropyl, butyl and hexyl groups, etc. The organic acids include oxalic acid, lactic acid, tartaric acid, citric acid, malic acid, malonic acid, succinic acid, glutaric acid, adipic acid, pimelic acid, sebacic acid, azelaic acid, etc.

As specific examples of the N,N-di-lower alkylhydroxylamine salts, may be mentioned diethylhydroxylammonium citrate, bis(diethylhydroxylammonium) tartrate, bis(diethylhydroxylammonium) adipate and bis-dibutylhydroxylamine sebacate.

(6) N-Hydrocarbyloxy-substituted, hindered amine compounds disclosed in Japanese Patent Application Laid-Open No. 233905/1992; heterocyclic compounds such as phenothiazine, and primary, secondary or tertiary hydroxylamine compounds disclosed in Japanese Patent Application Laid-Open No. 233906/1992; N-oxycarbamoyl-substituted, hindered amine compounds disclosed in Japanese Patent Application Laid-Open No. 233907/1992; and N-OH compounds such as N-(1-hydroxy-2,2,6,6-tetramethylpiperidin-4-yl) caprolactam, bis(1-hydroxy-2,2,6,6-tetramethylpiperidin-4-yl) sebacate, 1-hydroxy-2,2,6,6-tetramethylpiperidin-4-yl benzoate and 1-hydroxy-2,2,6,6-tetramethylpiperidin-4-yl acrylate disclosed In Japanese Patent Application Laid-Open No. 288302/1992 may be used.

As typical compounds of these compounds, may be mentioned respective compounds represented by the formula (IV):

(IV)

wherein the nitrogen atom is bonded directly to 2 tetrasubstituted carbon atoms, $E_1$, $E_2$, $E_3$ and $E_4$ are independently an organic group, and X is a divalent linking group; and the formula (V):

(V)

wherein the nitrogen atom is bonded directly to 2 tetrasubstituted carbon atoms, $E_1$, $E_2$, $E_3$ and $E_4$ are independently an organic group, and X is a divalent linking group.

In these formulae, $E_1$, $E_2$, $E_3$ and $E_4$ are preferably methyl groups. X is preferably a divalent organic group such as —COO—$(CH_2)_n$—COO— (n=1 to 20). As a preferable example of such a compound, may be mentioned bis(1-hydroxy-2,2,6,6-tetramethylpiperidin-4-yl) sebacate represented by the following formula (VI):

(VI)

(7) Nitrite

Nitrites such as sodium nitrite ($NaNO_2$) are inorganic precursors compounds capable of forming an NO radical in situ in a system to which the polymerization inhibitor has been added. Sodium nitrite is particularly effective in combined use with an inorganic phosphorus-containing compound such as sodium dihydrogenphosphate, phosphate type surfactant, tris(nonylphenyl)phosphite or the like which will be described subsequently.

Incidentally, among the above-mentioned compounds, the compounds (1) and (6) may overlap each other in some cases. Many of the above-described compounds are publicly known as agents for inhibiting premature polymerization of various kinds of monomers, or the like. However, the investigation by the present inventors have revealed that these compounds is not sufficient as polymerization inhibitor for various kinds of monomers such as conjugated dienes. The feature of the present invention resides in that such a compound (a) is used in combination with a phosphorus-containing compound (b).

Phosphorus-containing Compound (b)

No particular limitation is imposed on the phosphorus-containing compound (b). However, examples thereof include ① phosphoric compounds selected from the group consisting of phosphoric acid, phosphonic acid, phosphinic acid, diphosphonic acid, diphosphoric acid, hypophosphoric acid, diphosphoric acid, tripolyphosphoric acid and metaphosphoric acid; ② esterified products of the phosphoric compounds; ③ alkali metal salts or ammonium salts of the phosphoric compounds; ④ compounds obtained by introducing an ester linkage and an alkali metal salt linkage or an ammonium salt linkage into the phosphoric compounds; ⑤ phosphine compounds; and ⑥ hexaalkyl-phosphorus triamides. More specifically, as examples of the phosphorus-containing compounds, may be mentioned the following compounds:

<Phosphoric Compounds>

(1) Phosphoric acid (1)

(2) Phosphonic acid (phosphorous acid)

(2)

Phosphonic acid is a dibasic acid (left formula) of phosphorus having an oxidation number of 3 having a P—H linkage. The presence of a tautomer (right formula) may also be considered.

(3) Phosphinic acid (hypophosphorous acid)

(3)

Phosphinic acid is a monobasic acid (left formula) of phosphorus having an oxidation number of 1. The presence of a tautomer (right formula) may also be considered.

(4) Diphosphonic acid (diphosphorous acid)

(4)

(5) Hypophosphoric acid (5)

(6) Pyrophosphoric acid (diphosphoric acid)

(6)

(7) Tripolyphosphoric acid (triphosphoric acid)

(7)

(8) Metaphosphoric acid (8)

<Esterified products of phosphoric compounds>

(1) Alkyl dihydrogenphosphates $$\begin{array}{c} RO\diagdown\;\;\diagup OH \\ P \\ HO\diagup\;\;\diagdown O \end{array} \qquad (9)$$

R includes not only a hydrocarbon group such as an alkyl, phenyl or alkylphenyl group, but also a hydrophobic group, for example, an alkylphenyl, polyethylene oxide or alkylphenylpolyethylene oxide group, or the like. Regarding this, the same shall apply to the following compounds.

(2) Dialkyl dihydrogenphosphates $$\begin{array}{c} RO\diagdown\;\;\diagup OR \\ P \\ HO\diagup\;\;\diagdown O \end{array} \qquad (10)$$

(3) Trialkyl phosphates $$\begin{array}{c} RO\diagdown\;\;\diagup OR \\ P \\ RO\diagup\;\;\diagdown O \end{array} \qquad (11)$$

Besides the above compounds, esters of various kinds of phosphoric compounds, for example, phosphonates such as dimethyl phosphonate, diethyl phosphonate, triethyl phosphonate, triisopropyl phosphonate and triphenyl phosphonate; and metaphosphates, are included.

The phosphonates are phosphorus-containing compounds represented by the following formulae (12) to (14):

$$HP(O)(OH)(OR) \qquad (12)$$

$$HP(O)(OR)_2 \qquad (13)$$

$$P(OR)_3 \qquad (14)$$

Specific examples of the esterified products of the phosphoric compounds include triphenyl phosphate represented by the formula (15):

$$\begin{array}{c} (C_6H_5-O)\diagdown\;\;\diagup(O-C_6H_5) \\ P \\ (C_6H_5-O)\diagup\;\;\diagdown O \end{array} \qquad (15)$$

and tris(nonylphenyl)phosphite represented by the formula (16):

$$(C_9H_{19}-C_6H_4-O)P \qquad (16)$$

As the esterified products of the phosphorus-containing compounds having a hydrophobic group, may be mentioned various kinds of phosphate type surfactants. Among these, phosphate type surfactants generally used as rust preventives are particularly preferred because they combines an inhibitory effect on the formation of a popcorn polymer and a rubbery polymer with a rust-preventing effect. Specific examples of such phosphate type surfactants include alkyl dihydrogenphosphates represented by the formula (17):

$$R^1-\!\!\!\!\bigcirc\!\!\!\!-O\!\!-\!\!(C_2H_4O)_{n-1}\!\!-\!\!C_2H_4OP(O)(OH)_2 \qquad (17)$$

wherein $R^1$ is an alkyl group having generally 7 to 18 carbon atoms, often 8 or 9 carbon atoms, and n is the average number of moles added and generally 1 to 18, often 2 to 8, dialkyl hydrogenphosphates represented by the formula (18):

$$\left[ R^1-\!\!\!\!\bigcirc\!\!\!\!-O\!\!-\!\!(C_2H_4O)_{n-1}\!\!-\!\!C_2H_4O \right]_2 P(O)(OH) \qquad (18)$$

wherein $R^1$ is an alkyl group having generally 7 to 18 carbon atoms, often 8 or 9 carbon atoms, and n is the average number of moles added and generally 1 to 18, often 2 to 8, and phosphates represented by the formula (19):

$$[R^1-\!(C_2H_4O)_{n-1}\!-\!C_2H_4O]_m P(O)(OH)_{3-m} \qquad (19)$$

wherein $R^1$ is an alkyl group having generally 7 to 18 carbon atoms, often 8 or 9 carbon atoms, n is the average number of moles added and generally 1 to 18, often 2 to 8, and m is an integer of 1 to 3. More specifically, examples of the phosphate type surfactants include phosphate mixtures (for example, Ratemul P-909, product of Kao Corporation) represented by the formula (20):

$$\begin{array}{c} RO\diagdown\;\diagup OH \quad\quad RO\diagdown\;\diagup OH \\ P \quad\quad + \quad\quad P \\ HO\diagup\;\diagdown O \quad\quad RO\diagup\;\diagdown O \end{array} \qquad (20)$$

R: $C_9H_{19}-C_6H_4-O-(C_2H_4O)_8-C_2H_4-$ such as polyoxyethylene nonyl phenyl ether phosphates, and trialkyl phosphates (for example, Perex RP, product of Kao Corporation) represented by the formula (21):

$$\begin{array}{c} RO\diagdown\;\;\diagup OR \\ P \\ RO\diagup\;\;\diagdown O \end{array} \qquad (21)$$

R: $CH_3(CH_2)_3-\underset{\underset{C_2H_5}{|}}{CH}CH_2O-(C_2H_4O)_{n-1}-C_2H_4-$ wherein n is 2 to 6.

<Alkali Metal Salts or Ammonium Salts of Phosphoric Compounds>

(1) Primary phosphates

$$\begin{array}{c} MO\diagdown\;\;\diagup OH \\ P \\ HO\diagup\;\;\diagdown O \end{array} \qquad (22)$$

wherein M is an alkali metal such as Na or K, or an ammonium group. The same shall apply to the following salts.

(2) Secondary phosphates (23)

(3) Tertiary phosphates (24)

Specific examples of the secondary phosphates include sodium dihydrogenphosphate (Na dihydrogen-phosphate) represented by the formula (25):

(25)

Alkali metal salts or ammonium salts of various kinds of phosphoric compounds other than the above may also be used. A mixed salt with an alkali metal and an ammonium group bonded to the same phosphoric compound may also be used.

Specific examples of the alkali metal salts of the other phosphoric compounds include sodium metaphosphate represented by the formula (26):

(26)

wherein n is generally 3 to 16, and when n is 6, the compound is sodium hexametaphosphate, and sodium tripolyphosphate represented by the formula (27):

(27)

In addition, examples of the alkali metal salts or ammonium salts of the phosphoric compounds include potassium phosphate, ammonium hydrogenphosphate, potassium pyrophosphate, sodium pyrophosphate, potassium tripolyphosphate and sodium tripolyphosphate.

<Compounds Obtained by Introducing an Ester Linkage and an Alkali Metal Salt Linkage or an Ammonium Salt Linkage into Phosphoric Compounds>

(1) Dialkyl phosphate salts (28)

In the formula, R is an alkyl group, phenyl group, alkylphenyl group or such a hydrophobic group as described above, or the like, and M is an alkali metal or ammonium group. The same shall apply to the following formulae.

(2) Monoalkyl phosphate disalts (29)

Specific examples of these compounds include dipotassium monoalkyl phosphates represented by the formula (30):

(30)

and potassium dialkyl phosphates represented by the formula (31):

(31)

Specific examples of these compounds also include potassium 2-ethylhexyl pyrophosphate and sodium 2-ethyl-hexyl pyrophosphate

<Phosphine Compounds>

Examples of the phosphine compounds include triphenylphosphine [$(C_6H_6)_3P$] and triethylphosphine [$(C_2H_5)_3P$] represented by the formula (32):

$$(R)_3P \qquad (32)$$

<Hexaalkylphosphorus Triamides>

As the phosphorus-containing compound, may be used a hexaalkylphosphorus triamide represented by the formula (33.):

(33)

When R in the formula is a methyl group, the compound is hexamethylphosphorus triamide.

As the phosphorus-containing compounds used in the present invention, the phosphoric compounds, alkali metal salts or ammonium salts of the phosphoric compounds, tris(nonylphenyl)phosphite and hexamethylphosphorus triamide are preferred, with the phosphoric compounds and alkali metal salts or ammonium salts of the phosphoric compounds being particularly preferred.

The compound (a) and the phosphorus-containing compound (b) used in combination as the polymerization inhibitor according to the present invention are both stable, excellent in solubility in hydrocarbon mixtures and extraction solvents and good in handling property because they are liquid in many cases. The polymerization inhibitor according to the present invention is excellent in anticorrosion in many cases, and so it can also inhibit the formation of a popcorn polymer by iron rust in addition to the fact that it is hard to corrode apparatus.

A weight ratio of the compound (a) to the phosphorus-containing compound (b) is 1:10 to 100:1, preferably 1:1 to 80:1, more preferably 1:2 to 70:1. If the proportions of the compound (a) and phosphorus-containing compound (b) used are outside the above range, it is difficult to bring about the synergistic effect of both compounds.

When the polymerization inhibitor according to the present invention is used in a process for isolating and purifying a conjugated diene from a conjugated diene-containing hydrocarbon mixture, examples of a method for using the polymerization inhibitor include ① a method in which the polymerization inhibitor is added to the conjugated diene-containing hydrocarbon mixture fed to extractive distillation, ② a method in which the polymerization inhibitor is added to an extraction solvent, and ③ a method in which the polymerization inhibitor is added to a mixture of the hydrocarbon mixture and the extraction solvent in an extractive distillation column. The polymerization inhibitor is preferably continuously fed from the side of an extractive distillation column (first extractive distillation column) at a position higher than a plate in the extractive distillation column, to which an extraction solvent is fed, or an inlet or outlet of a condenser provided on the top of the extractive distillation column. The polymerization inhibitor may also be fed to a second extractive distillation column and other fractional distillation columns as needed. Feeding methods include such methods that a solution obtained by dissolving a prescribed amount of the polymerization inhibitor in the hydrocarbon mixture or extraction solvent is sprayed or added dropwise. The polymerization inhibitor according to the present invention may be used by adding it to a monomer, monomer mixture, monomer-containing hydrocarbon mixture or the like. The polymerization inhibitor according to the present invention may be used either by mixing the compound (a) with the compound (b) and then adding the resultant mixture or by separately adding the compound (a) and the compound (b).

The polymerization inhibitor according to the present invention is used in an amount sufficient to inhibit premature polymerization. When the polymerization inhibitor is used in, for example, a purifying process of a conjugated diene by extractive distillation, the amount of the polymerization inhibitor is generally 0.1 to 2,000 ppm, preferably 50 to 1,000 ppm based on the total weight of the conjugated diene-containing hydrocarbon mixture and the extraction solvent. When oxygen is present in plenty in the system upon the extractive distillation, a polymer is formed and deposited on a condenser and the like to contaminate the apparatus. Since the mixing of oxygen is unavoidable, it is preferred that an oxygen concentration in a gas phase discharged from the extractive distillation column be controlled by, for example, adding an oxygen scavenger to the extraction solvent so as to be of the order of generally 1 to 300 ppm, preferably 5 to 200 ppm, more preferably 5 to 100 ppm.

The polymerization inhibitor according to the present invention may also be suitably used in a process for recovering an olefin hydrocarbon compound such as ethylene, propylene, butene, butadiene or a mixture thereof after gas and liquid cracking or decomposing processes. More specifically, in a process for separating an organic feed flow containing an olefin hydrocarbon compound selected from among ethylene, propylene, butene, butadiene and mixtures thereof, and other unsaturated olefin compounds into a flow of the olefin hydrocarbon compound from the top of the column and a flow containing the other unsaturated olefin hydrocarbon compounds from the bottom of the column, the polymerization inhibitor according to the present invention is used by adding it into the organic feed flow. A proportion of the polymerization inhibitor according to the present invention used is generally selected from a range of 0.1 to 2,000 ppm based on the weight of the organic feed flow.

The polymerization inhibitor according to the present invention may also be used by adding it to a monomer such as a conjugated diene, aromatic vinyl, ethylenically unsaturated nitrile or α-olefin, or a mixture of the monomers. Even in this case, a proportion of the polymerization inhibitor used is generally selected from a range of 0.1 to 2,000 ppm based on the weight of the monomer or the mixture of the monomers.

Other polymerization inhibitors, chain transfer agents, oxygen scavengers and the like may be used upon the use of the polymerization inhibitor according to the present invention within limits not impeding the objects of the present invention. The polymerization inhibitor according to the present invention may be used by mixing both components. However, both components may be separately added into such various systems as described above.

EXAMPLES

The present invention will hereinafter be described more specifically by the following Examples and Comparative Examples.

Example 1

A flow from the bottom of a first extractive distillation column, which had been obtained by subjecting a $C_5$ hydrocarbon fraction to extractive distillation with DMF in the first distillation column, i.e., an extract (more soluble extract) containing isoprene and substances (easily soluble hydrocarbons) higher in solubility in the solvent than isoprene, was used as "a conjugated-diene containing hydrocarbon mixture" to conduct the following experiment. The concentration of isoprene in the extract is about 15 wt. %.

A 100-ml pressure glass container was charged with 20 g of the extract, 180 ppm in total of oxygen (added 3 times in an amount of 60 ppm every 8 hours), iron pieces (used for evaluating corrosive property) and a polymerization inhibitor and closed to conduct a reaction at 125° C. for 24 hours.

With respect to the polymerization inhibitor, N,N-diethylhydroxylamine (DEHA) was used as the compound (a). As the phosphorus-containing compound, was used a phosphate mixture (Ratemul P-909, product of Kao Corporation) represented by the formula (20):

which is a phosphate type surfactant (rust preventive). The respective components of the polymerization inhibitor were added 3 times each in an amount of 480 ppm every 8 hours.

After the reaction, the contents were filtered through filter paper, and a product obtained by drying solids remaining on the filter paper was regarded as "Polymer", while residue obtained by drying a filtrate was regarded as "High Boil". Both products are polymers formed by polymerization of isoprene, and "High Boil" is comparatively low in polymerization degree and hence corresponds to a rubbery polymer. The amounts of Polymer and High Boil were measured to calculate out their weight proportions (wt. %) to the amount of isoprene. On the other hand, change in the iron pieces was observed to evaluate the degree of corrosion. The unit is mg/dm$^2$ day (weight loss, mg on corrosion for a day per 100 cm$^2$). The results are shown in Table 1.

Comparative Examples 1 to 4

Respective reactions were conducted in the same manner as in Example 1 except that the polymerization inhibitor was changed to their corresponding kinds and amounts added shown in Table 1. However, in Comparative Example 2, 2.5% furfural was first added. In Comparative Examples 3 and 4, the respective components were added 3 times each in an amount of 480 ppm every 8 hours. The results are shown in Table 1.

TABLE 1

| | Polymerization inhibitor | Polymer (%) | High Boil (%) | Total (%) | Corrosion (mg/dm$^2$ · day) |
|---|---|---|---|---|---|
| Ex. 1 | DEHA/phosphorus-containing compound (each 480 ppm/time) | 0.07 | 0.25 | 0.32 | 0.0 |
| Comp. Ex. 1 | Not added | 1.00 | 0.08 | 1.08 | 1.5 |
| Comp. Ex. 2 | Furfural (2.5%/system) | 0.32 | 0.16 | 0.48 | 3.0 |
| Comp. Ex. 3 | DEHA (480 ppm/time) | 0.70 | 0.11 | 0.81 | 0.0 |
| Comp. Ex. 4 | DEHA/oxalic acid (1:2 mol) (480 ppm/time) | 0.06 | 0.27 | 0.33 | 25.5 |

(Note)
(1) A DMF solution of crude isoprene (more soluble extract) was used.
(2) Oxygen = 60 ppm.
(3) Reaction conditions = 125° C. × 24 hours.
(4) DEHA: N,N-diethylhydroxylamine.

As apparent from the results shown in Table 1, the polymerization reaction of isoprene is inhibited, and moreover no corrosion is caused when the polymerization inhibitor according to the present invention is used (Example 1). On the other hand, when no polymerization inhibitor is added (Comparative Example 1), the formation of a polymer is marked. When furfural proposed in the prior art was used (Comparative Example 2), the inhibitory effect on polymerization reaction was little, and corrosive property was recognized though it was extremely slight. When DEHA is used by itself (Comparative Example 3), the inhibitory effect on polymerization reaction is insufficient. When DEHA and oxalic acid are used in combination (Comparative Example 4), the inhibitory effect on polymerization reaction is good, but corrosive property is recognized, so that it is expected to form a popcorn polymer due to iron rust.

Examples 2 to 5, and Comparative Examples 5 to 20

Respective experiments were conducted in the same manner as in Example 1 except that ① a DMF solution of purified isoprene (isoprene concentration=15 wt. %) was used in place of the DMF solution of crude isoprene, ② no iron piece was added, ③ the polymerization inhibitor was changed to their corresponding kinds and quantity proportions shown in Table 2, ④ the concentration of oxygen was changed from 60 ppm to 180 ppm, and ⑤ the reaction conditions were changed from 125° C. for 24 hours to 100° C. for 3 days. However, the respective components were first added to the system in their corresponding amounts shown in Table 2. Incidentally, in Comparative Example 5, neither oxygen nor polymerization inhibitor was added. In other Examples and Comparative Examples, oxygen was added in an amount of 180 ppm. The results are shown in Table 2.

TABLE 2

| | Polymerization inhibitor | Polymer (%) | High Boil (%) | Total (%) |
|---|---|---|---|---|
| Ex. 2 | DEHA (180 ppm)/phosphoric acid (180 ppm) | 0.04 | 0.06 | 0.10 |
| Ex. 3 | DEHA (360 ppm)/phosphoric acid (180 ppm) | 0.01 | 0.08 | 0.09 |
| Ex. 4 | DEHA (180 ppm)/Na dihydrogenphosphate (180 ppm) | 0.01 | 0.06 | 0.07 |
| Ex. 5 | DEHA (360 ppm)/Na dihydrogenphosphate (180 ppm) | 0.01 | 0.06 | 0.07 |
| Comp. Ex. 5 | Not added (oxygen was also not added) | 0.06 | 0.12 | 0.18 |
| Comp. Ex. 6 | Only oxygen (180 ppm) was added | 0.54 | 0.08 | 0.62 |
| Comp. Ex. 7 | Furfural (2.5%) | 0.26 | 0.12 | 0.38 |
| Comp. Ex. 8 | DEHA (180 ppm) | 0.19 | 0.09 | 0.28 |
| Comp. Ex. 9 | Phosphoric acid (180 ppm) | 0.41 | 0.07 | 0.48 |
| Comp. Ex. 10 | Phosphoric acid (360 ppm) | 0.26 | 0.08 | 0.34 |
| Comp. Ex. 11 | Na dihydrogenphosphate (180 ppm) | 0.09 | 0.32 | 0.41 |
| Comp. Ex. 12 | Na dihydrogenphosphate (360 ppm) | 0.13 | 0.28 | 0.41 |
| Comp. Ex. 13 | Hydroquinone (180 ppm) | 0.41 | 0.48 | 0.89 |
| Comp. Ex. 14 | TBC (180 ppm) | 0.04 | 0.31 | 0.35 |
| Comp. Ex. 15 | BHT (180 ppm) | 0.61 | 0.10 | 0.71 |
| Comp. Ex. 16 | Monoethanolamine (180 ppm) | 0.38 | 0.40 | 0.78 |
| Comp. Ex. 17 | Hydroquinone (180 ppm)/phosphoric acid (180 ppm) | 0.34 | 0.11 | 0.45 |
| Comp. Ex. 18 | TBC (180 ppm)/phosphoric acid (180 ppm) | 0.18 | 0.06 | 0.24 |
| Comp. Ex. 19 | BHT (180 ppm)/phosphoric acid (180 ppm) | 0.35 | 0.07 | 0.42 |
| Comp. Ex. 20 | Monoethanolamine (180 ppm)/phosphoric acid (180 ppm) | 0.38 | 0.10 | 0.48 |

(Note)
(1) A DMF solution of purified isoprene was used.
(2) Oxygen = 180 ppm.
(3) Reaction conditions = 100° C. × 3 days.
(4) DEHA: N,N-diethylhydroxylamine.
(5) TBC: 4-t-butylcatechol.
(6) BHT: 2,6-di-t-butyl-4-methylphenol.

As apparent from the results shown in Table 2, it is understood that when the polymerization inhibitors according to the present invention are used (Examples 2 to 5), the polymerization reaction is markedly inhibited. On the other hand, when no polymerization inhibitor is used (Comparative Examples 5 and 6), or the conventional polymerization inhibitors or polymerization inhibitors having a composition outside the range according to the present invention are used (Comparative Examples 7 to 20), no sufficient inhibitory effect on polymerization reaction cannot be achieved. Accordingly, it can be understood that when the method according to the present invention is applied to an actual distillation process including extractive distillation, an excellent inhibitory effect on the formation of a popcorn polymer and a rubbery polymer is brought about.

Example 6

Twenty grams of a dimethylformamide (DMF) solution (isoprene concentration=15 wt. %) of purified isoprene (purity: 99.3%) were placed in a 100-ml pressure glass container, and 180 ppm in total of oxygen (added 3 times in an amount of 60 ppm every 8 hours), 90 ppm of sodium nitrite and 90 ppm of sodium dihydrogenphosphate were charged therein. After the container was closed, a reaction was conducted at 100° C. for 3 days. Oxygen is added for the purpose of accelerating the reaction. After the reaction, the proportions of Polymer and High Boil formed were calculated out. The results are shown in Table 3.

Examples 7 and Comparative Examples 21 to 24

The same procedure as in Example 6 was followed except that the kind and amount added of the polymerization inhibitor were respectively changed as shown in Table 3. However, in Comparative Example 21, no polymerization inhibitor was added, but only oxygen was added. In Comparative Examples 22 to 24 and Example 7, 180 ppm of oxygen were also added in the same manner as in Example 6. The results are shown in Table 3.

TABLE 3

| | Polymerization inhibitor | Polymer (%) | High Boil (%) | Total (%) |
|---|---|---|---|---|
| Comp. Ex. 21 | Oxygen (180 ppm) | 0.46 | 0.21 | 0.67 |
| Comp. Ex. 22 | Na dihydrogenphosphate (180 ppm) | 0.03 | 0.27 | 0.30 |
| Comp. Ex. 23 | Na nitrite (90 ppm) | 0.02 | 0.14 | 0.16 |
| Comp. Ex. 24 | Na nitrite (180 ppm) | 0.02 | 0.12 | 0.14 |
| Ex. 6 | Na nitrite (90 ppm)/Na dihydrogenphosphate (90 ppm) | 0.01 | 0.06 | 0.07 |
| Ex. 7 | Na nitrite (180 ppm)/Na dihydrogenphosphate (180 ppm) | 0.01 | 0.06 | 0.07 |

As apparent from the results shown in Table 3, it is understood that when the compound (a) and the phosphorus-containing compound (b) were used in combination as a polymerization inhibitor (Examples 6 and 7), the polymerization of isoprene was markedly inhibited compared with the results of Comparative Examples 21 to 24.

Example 8

Twenty grams of a DMF solution (butadiene concentration=15 wt. %) of purified butadiene (purity: 99.2%) were placed in a 100-ml pressure glass container, and 180 ppm in total of oxygen (added 3 times in an amount of 60 ppm every 8 hours), 120 ppm of sodium nitrite and 120 ppm of sodium dihydrogenphosphate were charged therein. After the container was closed, a reaction was conducted at 100° C. for 3 days. After the reaction, the amounts of Polymer and High Boil formed were measured in the same manner as in Example 1 to calculate out their proportions (wt. %) to the amount of butadiene. The results are shown in Table 4.

Comparative Examples 25 and 26

The same procedure as in Example 8 was followed except that the kind and amount added of the polymerization inhibitor were respectively changed as shown in Table 4. However, in Comparative Example 25, no polymerization inhibitor was added, but only oxygen was added. In Comparative Example 26, 180 ppm of oxygen were also added in the same manner as in Example 8. The results are shown in Table 4.

TABLE 4

| | Polymerization inhibitor | Polymer (%) | High Boil (%) | Total (%) |
|---|---|---|---|---|
| Comp. Ex. 25 | Oxygen (180 ppm) | 0.29 | 0.08 | 0.37 |
| Comp. Ex. 26 | Na nitrite (120 ppm) | 0.05 | 0.12 | 0.17 |
| Ex. 8 | Na nitrite (120 ppm)/Na dihydrogenphosphate (120 ppm) | 0.01 | 0.08 | 0.09 |

As apparent from the results shown in Table 4, it is understood that when the compound (a) and the phosphorus-containing compound (b) were used in combination as a polymerization inhibitor (Example 8), the polymerization of butadiene was markedly inhibited compared with the results of Comparative Examples 25 to 26.

Example 9

Twenty grams of a DMF solution (butadiene concentration=15 wt. %) of purified butadiene (purity: 99.2%) were placed in a 100-ml pressure glass container, and 180 ppm in total of oxygen (added 3 times in an amount of 60 ppm every 8 hours), 90 ppm of sodium nitrite and 90 ppm of sodium dihydrogenphosphate were charged therein. After the container was closed, a reaction was conducted at 100° C. for 3 days. After the reaction, the proportions of Polymer and High Boil formed were calculated out. The results are shown in Table 5.

Comparative Examples 27 and 28

The same procedure as in Example 9 was followed except that the kind and amount added of the polymerization inhibitor were respectively changed as shown in Table 5. However, in Comparative Example 27, no polymerization inhibitor was added, but only oxygen was added. In Comparative Example 28, 180 ppm of oxygen were also added in the same manner as in Example 9. The results are shown in Table 4.

TABLE 5

|  | Polymerization inhibitor | Polymer (%) | High Boil (%) | Total (%) |
|---|---|---|---|---|
| Comp. Ex. 27 | Oxygen (180 ppm) | 0.29 | 0.06 | 0.35 |
| Comp. Ex. 28 | Na nitrite (90 ppm) | 0.04 | 0.09 | 0.13 |
| Ex. 9 | Na nitrite (90 ppm)/Na dihydrogenphosphate (90 ppm) | 0.01 | 0.05 | 0.06 |

As apparent from the results shown in Table 5, it is understood that when the compound (a) and the phosphorus-containing compound (b) were used in combination as a polymerization inhibitor (Example 8), the polymerization of butadiene was markedly inhibited compared with the results of Comparative Examples 27 to 28 even when the amounts of these compounds added were small.

Example 10

Twenty grams of a DMF solution (isoprene concentration=15 wt. %) of purified isoprene were placed in a 100-ml pressure glass container, and 180 ppm in total of oxygen (added 3 times in an amount of 60 ppm every 8 hours), 180 ppm of 4-oxo-2,2,6,6-tetramethylpiperidine-1-oxyl and 180 ppm of sodium dihydrogenphosphate were charged therein. After the container was closed, a reaction was conducted at 100° C. for 3 days. After the reaction, the proportions of Polymer and High Boil formed were calculated out. The results are shown in Table 6.

Example 11 and Comparative Examples 29 to 32

The same procedure as in Example 10 was followed except that the kind and amount added of the polymerization inhibitor were respectively changed as shown in Table 6. However, in Comparative Example 29, no polymerization inhibitor was added, but only oxygen was added. In Comparative Examples 30 to 32 and Example 11, 180 ppm of oxygen were also added in the same manner as in Example 10. The results are shown in Table 6.

TABLE 6

|  | Polymerization inhibitor | Polymer (%) | High Boil (%) | Total (%) |
|---|---|---|---|---|
| Comp. Ex. 29 | Oxygen (180 ppm) | 0.39 | 0.19 | 0.58 |
| Comp. Ex. 30 | Na dihydrogenphosphate (180 ppm) | 0.02 | 0.29 | 0.31 |
| Comp. Ex. 31 | 4-Oxo-2,2,6,6-tetramethyl-piperidine-1-oxyl (180 ppm) | 0.37 | 0.06 | 0.43 |
| Comp. Ex. 32 | 4-Hydroxy-2,2,6,6-tetramethyl-piperidine-1-oxyl (180 ppm) | 0.22 | 0.06 | 0.28 |
| Ex. 10 | 4-Oxo-2,2,6,6-tetramethyl-piperidine-1-oxyl (180 ppm)/Na dihydrogenphosphate (180 ppm) | 0.02 | 0.06 | 0.08 |
| Ex. 11 | 4-Hydroxy-2,2,6,6-tetramethyl-piperidine-1-oxyl (180 ppm)/Na dihydrogenphosphate (180 ppm) | 0.01 | 0.05 | 0.06 |

As apparent from the results shown in Table 6, it is understood that when the compound (a) and the phosphorus-containing compound (b) were used in combination as a polymerization inhibitor (Examples 10 and 11), the polymerization of isoprene was markedly inhibited compared with the results of Comparative Examples 29 to 32.

Example 12

Twenty grams of a DMF solution (isoprene concentration=15 wt. %) of purified isoprene were placed in a 100-ml pressure glass container, and 180 ppm in total of oxygen (added 3 times in an amount of 60 ppm every 8 hours), 180 ppm of nitrosophenylhydroxyamine ammonium salt and 180 ppm of sodium dihydrogenphosphate were charged therein. After the container was closed, a reaction was conducted at 100° C. for 3 days. After the reaction, the proportions of Polymer and High Boil formed were calculated out in the same manner as in Example 1. The results are shown in Table 7.

Comparative Examples 33 and 35

The same procedure as in Example 12 was followed except that the kind and amount added of the polymerization inhibitor were respectively changed as shown in Table 7. However, in Comparative Example 33, no polymerization inhibitor was added, but only oxygen was added. In Comparative Examples 34 and 35, 180 ppm of oxygen were also added in the same manner as in Example 12. The results are shown in Table 7.

TABLE 7

|  | Polymerization inhibitor | Polymer (%) | High Boil (%) | Total (%) |
|---|---|---|---|---|
| Comp. Ex. 33 | Oxygen (180 ppm) | 0.22 | 0.06 | 0.28 |
| Comp. Ex. 34 | Na dihydrogenphosphate (180 ppm) | 0.13 | 0.24 | 0.37 |
| Comp. Ex. 35 | Nitrosophenylhydroxyamine ammonium salt (180 ppm) | 0.26 | 0.07 | 0.33 |
| Ex. 12 | Nitrosophenylhydroxyamine ammonium salt (180 ppm)/Na dihydrogenphosphate (180 ppm) | 0.09 | 0.05 | 0.14 |

As apparent from the results shown in Table 7, it is understood that when the compound (a) and the phosphorus-containing compound (b) were used in combination as a polymerization inhibitor (Example 12), the polymerization of isoprene was markedly inhibited compared with the results of Comparative Examples 33 to 35.

Example 13

Twenty grams of a DMF solution (isoprene concentration=15 wt. %) of purified isoprene were placed in a 100-ml pressure glass container, and 180 ppm in total of oxygen (added 3 times in an amount of 60 ppm every 8 hours), 180 ppm of sodium nitrite and 180 ppm of sodium dihydrogenphosphate were charged therein. After the container was closed, a reaction was conducted at 100° C. for 3 days.

After the reaction, the proportions of Polymer and High Boil formed were calculated out in the same manner as in Example 1. The results are shown in Table 8.

Example 14

The experiment was conducted in the same manner as in Example 13 except that Perex RP (sesquipolyethylene-2- ethylhexyl phosphate) produced by Kao Corporation was used in place of sodium dihydrogenphosphate. The results are shown in Table 8.

Example 15

The experiment was conducted in the same manner as in Example 13 except that tris(nonylphenyl)phosphite was used in place of sodium dihydrogenphosphate. The results are shown in Table 8.

Comparative Example 36

The experiment was conducted in the same manner as in Example 13 except that no polymerization inhibitor was added, but only oxygen was added. The results are shown in Table 8.

Comparative Example 37

The experiment was conducted in the same manner as in Example 13 except that 180 ppm of sodium nitrite were added as a polymerization inhibitor. The results are shown in Table 8.

TABLE 8

|  | Polymerization inhibitor | Polymer (%) | High Boil (%) | Total (%) |
|---|---|---|---|---|
| Comp. Ex. 36 | Oxygen (180 ppm) | 0.41 | 0.08 | 0.49 |
| Comp. Ex. 37 | Na nitrite (180 ppm) | 0.03 | 0.13 | 0.16 |
| Ex. 13 | Na nitrite (180 ppm)/Na dihydrogenphosphate (180 ppm) | 0.01 | 0.05 | 0.06 |
| Ex. 14 | Na nitrite (180 ppm)/Perex RP (180 ppm) | 0 | 0.06 | 0.06 |
| Ex. 15 | Na nitrite (180 ppm)/tris-(nonylphenyl)phosphite (180 ppm) | 0.01 | 0.07 | 0.08 |

As apparent from the results shown in Table 8, it is understood that when the compound (a) and the phosphorus-containing compound (b) were used in combination as a polymerization inhibitor (Examples 13 to 15), the polymerization of isoprene was markedly inhibited compared with the results of Comparative Examples 36 and 37.

Example 16

Twenty grams of a DMF solution (isoprene concentration=15 wt. %) of purified isoprene were placed in a 100-ml pressure glass container, and 180 ppm in total of oxygen (added 3 times in an amount of 60 ppm every 8 hours), 180 ppm of N,N-dimethylhydroxylamine (DEHA), 3.6 ppm of sodium dihydrogenphosphate and iron pieces were charged therein. After the container was closed, a reaction was conducted at 100° C. for 3 days. After the reaction, the proportions of Polymer and High Boil formed were calculated out in the same manner as in Example 1. The results are shown in Table 9.

Examples 17 to 21, and Comparative Examples 38 to 46

The reaction was conducted in the same manner as in Example 16 except that the polymerization inhibitor was changed to their corresponding kinds and amounts added shown in Table 9. The results are shown in Table 9.

TABLE 9

|  | Oxygen (ppm) | DEHA (ppm) | Phosphorus-containing compound Kind | (ppm) | Polymer (%) | High Boil (%) | Total (%) |
|---|---|---|---|---|---|---|---|
| Comp. Ex. 38 | — | — | Not added | — | 0.09 | 0.08 | 0.17 |
| Comp. Ex. 39 | 180 | — | Not added | — | 0.58 | 0.08 | 0.66 |
| Comp. Ex. 40 | 180 | 180 | Not added | — | 0.27 | 0.06 | 0.33 |
| Comp. Ex. 41 | 180 | — | Na dihydrogenphosphate | 180 | 0.05 | 0.23 | 0.28 |
| Comp. Ex. 42 | 180 | — | Hexamethylphosphorus triamide | 180 | 0.12 | 0.07 | 0.19 |
| Comp. Ex. 43 | 180 | — | Triphenylphosphine | 180 | 0.20 | 0.36 | 0.56 |
| Comp. Ex. 44 | 180 | — | Trimethyl phosphonate | 180 | 0.08 | 0.28 | 0.36 |
| Comp. Ex. 45 | 180 | — | Triphenyl phosphonate | 180 | 0.48 | 0.09 | 0.57 |
| Comp. Ex. 46 | 180 | — | Triethylphosphine | 180 | 0.27 | 0.25 | 0.52 |
| Ex. 16 | 180 | 180 | Na dihydrogenphosphate | 3.6 | 0.02 | 0.06 | 0.08 |
| Ex. 17 | 180 | 180 | Hexamethylphosphorus triamide | 18 | 0.04 | 0.04 | 0.08 |
| Ex. 18 | 180 | 180 | Triphenylphosphine | 18 | 0.02 | 0.07 | 0.09 |
| Ex. 19 | 180 | 180 | Trimethyl phosphonate | 18 | 0.06 | 0.04 | 0.10 |
| Ex. 20 | 180 | 180 | Triphenyl phosphonate | 18 | 0.05 | 0.09 | 0.14 |
| Ex. 21 | 180 | 180 | Triethylphosphine | 18 | 0.05 | 0.10 | 0.15 |

(Note)
(1) DEHA: N,N-diethylhydroxylamine.

As apparent from the results shown in Table 9, it is understood that when the compound (a) and the phosphorus-containing compound (b) were used in combination as a polymerization inhibitor (Examples 16 to 21), the polymerization of isoprene was markedly inhibited compared with the results of Comparative Examples 38 to 46. In addition, no corrosion of the iron pieces was observed in the respective Examples.

Example 22

Twenty grams of a DMF solution (isoprene concentration=15 wt. %) of purified isoprene were placed in a 100-ml pressure glass container, and 180 ppm in total of oxygen (added 3 times in an amount of 60 ppm every 8 hours), 180 ppm of 4-hydroxy-2,2,6,6-tetramethyl-piperidine-1-oxyl (HTPO), 180 ppm of hexamethylphosphorus triamide and iron pieces were charged therein. After the container was closed, a reaction was conducted at 100° C. for 3 days. After the reaction, the proportions of Polymer and High Boil formed were calculated out in the same manner as in Example 1. The results are shown in Table 10.

Examples 23 to 25, and Comparative Examples 47 to 49

The reaction was conducted in the same manner as in Example 22 except that the polymerization inhibitor was changed to their corresponding kinds and amounts added shown in Table 10. The results are shown in Table 10.

hydroxylamine (DEHA) and 50 ppm of Na dihydrogenphosphate were added. An air atmosphere was used as an atmosphere. After a reaction was conducted at 120° C. for 1 hour, the reaction mixture was dried to measure the amount of High Boil formed. The result is shown in Table 11.

Examples 27 and 28, and Comparative Examples 50 to 53

The reaction was conducted in the same manner as in Example 26 except that the polymerization inhibitor was changed to their corresponding kinds and amounts added shown in Table 11. The results are shown in Table 11.

TABLE 11

| | NO radical compound or precursor | | Na dihydrogen-phosphate | High Boil |
|---|---|---|---|---|
| | Kind | (ppm) | (ppm) | (%) |
| Comp. Ex. 50 | Not added | — | 0 | 10.40 |
| Comp. Ex. 51 | DEHA | 50 | 0 | 5.71 |
| Ex. 26 | DEHA | 50 | 50 | 1.79 |
| Comp. Ex. 52 | HTPO | 50 | 0 | 0.44 |
| Ex. 27 | HTPO | 50 | 50 | 0.17 |
| Comp. Ex. 53 | BOTS | 50 | 0 | 3.34 |

TABLE 10

| | Oxygen | HTPO | Phosphorus-containing compound | | Polymer | High Boil | Total |
|---|---|---|---|---|---|---|---|
| | (ppm) | (ppm) | Kind | (ppm) | (%) | (%) | (%) |
| Comp. Ex. 47 | — | — | Not added | — | 0.09 | 0.08 | 0.17 |
| Comp. Ex. 48 | 180 | — | Not added | — | 0.57 | 0.08 | 0.65 |
| Comp. Ex. 49 | 180 | 180 | Not added | — | 0.14 | 0.07 | 0.21 |
| Ex. 22 | 180 | 180 | Hexamethylphosphorus triamide | 180 | 0.00 | 0.02 | 0.02 |
| Ex. 23 | 180 | 180 | Triethylphosphine | 180 | 0.01 | 0.04 | 0.05 |
| Ex. 24 | 180 | 180 | Triphenylphosphine | 180 | 0.06 | 0.05 | 0.11 |
| Ex. 25 | 180 | 180 | Trimethyl phosphonate | 180 | 0.06 | 0.06 | 0.12 |

(Note)
(1) HTPO: 4-hydroxy-2,2,6,6-tetramethylpiperidine-1-oxyl.

As apparent from the results shown in Table 10, it is understood that when the compound (a) and the phosphorus-containing compound (b) were used in combination as a polymerization inhibitor (Examples 22 to 25), the polymerization of isoprene was markedly inhibited compared with the results of Comparative Examples 47 to 49. In addition, no corrosion of the iron pieces was observed in the respective Examples.

Example 26

After 500 ml of styrene were washed twice with 200 ml of 1N caustic soda and then twice with 200 ml of water, zeolite (Zeolite A-3, product of Tosoh Corp.) was poured therein to dry styrene. In this example, the washing and drying were respectively conducted by shaking the mixture containing styrene and the like for 2 to 3 minutes in a bottle.

Styrene purified above was taken out and charged into an ampoule. At this time, 50 ppm of N,N-diethyl- TABLE 11-continued

| | NO radical compound or precursor | | Na dihydrogen-phosphate | High Boil |
|---|---|---|---|---|
| | Kind | (ppm) | (ppm) | (%) |
| Ex. 28 | BOTS | 50 | 50 | 2.33 |

(Note)
(1) DEHA: N,N-diethylhydroxylamine.
(2) HTPO: 4-hydroxy-2,2,6,6-tetramethylpiperidine-1-oxyl.
(3) BOTS: bis(1-oxyl-2,2,6,6-tetramethylpiperidin-4-yl) sebacate.

As apparent from the results shown in Table 11, it is understood that when the compound (a) and the phosphorus-containing compound (b) were used in combination as a polymerization inhibitor (Examples 26 to 28), the polymerization of styrene was markedly inhibited compared with the results of Comparative Examples 50 to 53.

Examples 29 and 30, and Comparative Examples 54 and 55

The experiment was conducted in the same manner as in Example 26 except that the proportions of the compound (a) and Na dihydrogenphosphate used were changed as shown in Table 12, and the reaction was conducted at 120° C. for 3 hours. The results are shown in Table 12.

TABLE 12

| | NO radical compound or precursor | | Na dihydrogen-phosphate | High Boil |
|---|---|---|---|---|
| | Kind | (ppm) | (ppm) | (%) |
| Comp. Ex. 54 | HTPO | 500 | 0 | 1.63 |
| Ex. 29 | HTPO | 500 | 500 | 0.31 |
| Comp. Ex. 55 | BOTS | 500 | 0 | 2.54 |
| Ex. 28 | BOTS | 500 | 500 | 0.40 |

(Note)
(1) HTPO: 4-hydroxy-2,2,6,6-tetramethylpiperidine-1-oxyl.
(2) BOTS: bis(1-oxyl-2,2,6,6-tetramethylpiperidin-4-yl) sebacate.

As apparent from the results shown in Table 12, it is understood that when the compound (a) and the phosphorus-containing compound (b) were used in combination as a polymerization inhibitor (Examples 29 and 30), the polymerization of styrene was markedly inhibited compared with the results of Comparative Examples 54 and 55.

Industrial Applicability

According to the present invention, there are provided polymerization inhibitors, a polymerization-inhibiting method and polymerization-inhibiting compositions comprising a monomer and a polymerization inhibitor for inhibiting the occurrence of unfavorable premature polymerization in various operating steps such as the production, purification, storage, shipment, preparation and use of a monomer such as a conjugated diene, aromatic vinyl, ethylenically unsaturated nitrile or α-olefin, a mixture of the monomers or a hydrocarbon mixture containing the monomer.

The polymerization inhibitors according to the present invention are particularly effective for inhibiting the formation of a popcorn polymer and a rubbery polymer in a production process of a purified conjugated diene, comprising isolating the conjugated diene by conducting a distillation process including extractive distillation from a conjugated diene-containing hydrocarbon mixture.

What is claimed is:

1. A polymerization-inhibiting composition comprising at least one compound (a) selected from the group consisting of an N,N-dialkylhydroxylamine, a sterically hindered nitroxyl compound, a sterically hindered hydroxylamine compound and inorganic nitrate compound, a phosphorus-containing compound (b), and a conjugated diene-containing hydrocarbon mixture selected from the group consisting of an isoprene-containing $C_5$ hydrocarbon fraction and a 1,3-butadiene-containing $C_4$ hydrocarbon fraction, wherein a weight ratio of the compound (a) to the phosphorus-containing compound (b) is 1:10 to 100:1.

2. The polymerization-inhibiting composition according to claim 1, wherein the compound (a) is at least one compound selected from the group consisting of an N,N-dialkylhydroxylamine, a sterically hindered nitroxyl compound and a sterically hindered hydroxylamine compound.

3. The polymerization-inhibiting composition according to claim 2, wherein the N,N-dialkylhydroxylamine is a compound represented by the formula (I):

wherein $R_1$ and $R_2$ are independently a linear, branched or cyclic alkyl group having 1 to 10 carbon atoms.

4. The polymerization-inhibiting composition according to claim 2, wherein the sterically hindered nitroxyl compound is a compound represented by the formula (II):

wherein the nitrogen atom is bonded directly to 2 disubstituted carbon atoms, $E_1$, $E_2$, $E_3$ and $E_4$ are independently an organic group, and T is an organic group required to form a 5- or 6-membered ring, or a compound represented by the formula (IV):

wherein the nitrogen atom is bonded directly to 2 disubstituted carbon atoms, $E_1$, $E_2$, $E_3$ and $E_4$ are independently an organic group, and X is a divalent linking group.

5. The polymerization-inhibiting composition according to claim 2, wherein the sterically hindered hydroxylamine compound is a compound represented by the formula (III):

wherein the nitrogen atom is bonded directly to 2 disubstituted carbon atoms, $E_1$, $E_2$, $E_3$ and $E_4$ are independently an organic group, and T is an organic group required to form a 5- or 6-membered ring, or a compound represented by the formula (V):

(V)

wherein the nitrogen atom is bonded directly to 2 disubstituted carbon atoms, $E_1$, $E_2$, $E_3$ and $E_4$ are independently an organic group, and X is a divalent linking group.

6. The polymerization-inhibiting composition according to claim 1, wherein the phosphorus-containing compound (b) is at least one selected from the group consisting of phosphoric compounds, esterified products of the phosphoric compounds, alkali metal salts or ammonium salts of the phosphoric compounds, compounds obtained by introducing an ester linkage and an alkali metal salt linkage or an ammonium salt linkage into the phosphoric compounds, phosphine compounds, and hexaalkylphosphorus triamides.

7. A method for inhibiting polymerization, which comprises causing at least one compound (a) selected from the group consisting of a N,N-dialkylhydroxylamine, a sterically hindered nitroxyl compound, a sterically hindered hydroxylamine compound and inorganic nitrate compound, and a phosphorus-containing compound (b) to coexist at a weight ratio of the compound (a) to the phosphorus-containing compound (b) of 1:10 to 100:1 with a conjugated diene-containing hydrocarbon mixture selected from the group consisting of an isoprene-containing $C_5$ hydrocarbon fraction and a 1,3-butadiene-containing $C_4$ hydrocarbon fraction.

8. The polymerization-inhibiting method according to claim 7, wherein the compound (a) is at least one compound selected from the group consisting of an N,N-dialkylhydroxylamine, a sterically hindered nitroxyl compound and a sterically hindered hydroxylamine compound.

9. The polymerization-inhibiting method according to claim 8, wherein the N,N-dialkylhydroxylamine is a compound represented by the formula (I):

(I)

wherein $R_1$ and $R_2$ are independently a linear, branched or cyclic alkyl group having 1 to 10 carbon atoms.

10. The polymerization-inhibiting method according to claim 8, wherein the sterically hindered nitroxyl compound is a compound represented by the formula (II):

(II)

wherein the nitrogen atom is bonded directly to 2 disubstituted carbon atoms, $E_1$, $E_2$, $E_3$ and $E_4$ are independently an organic group, and T is an organic group required to form a 5- or 6-membered ring, or a compound represented by the formula (IV):

(IV)

wherein the nitrogen atom is bonded directly to 2 disubstituted carbon atoms, $E_1$, $E_2$, $E_3$ and $E_4$ are independently an organic group, and X is a divalent linking group.

11. The polymerization-inhibiting method according to claim 8, wherein the sterically hindered hydroxylamine compound is a compound represented by the formula (III):

(III)

wherein the nitrogen atom is bonded directly to 2 disubstituted carbon atoms, $E_1$, $E_2$, $E_3$ and $E_4$ are independently an organic group, and T is an organic group required to form a 5- or 6-membered ring, or a compound represented by the formula (V):

(V)

wherein the nitrogen atom is bonded directly to 2 disubstituted carbon atoms, $E_1$, $E_2$, $E_3$ and $E_4$ are independently an organic group, and X is a divalent linking group.

12. The polymerization-inhibiting method according to claim 7, wherein the phosphorus-containing compound (b) is at least one selected from the group consisting of phosphoric compounds, esterified products of the phosphoric compounds, alkali metal salts or ammonium salts of the phosphoric compounds, compounds obtained by introducing an ester linkage and an alkali metal salt linkage or an ammonium salt linkage into the phosphoric compounds, phosphine compounds, and hexaalkylphosphorus triamides.

13. The polymerization-inhibiting method according to claim 7, wherein the compound (a) and the phosphorus-containing compound (b) are caused to coexist with a conjugated diene in a preparation process of a purified conjugated diene, comprising isolating the conjugated diene by conducting a distillation process including extractive distillation from a conjugated diene-containing hydrocarbon mixture.

14. The polymerization-inhibiting method according to claim 8, wherein the phosphorus-containing compound (b) is at least one selected from the group consisting of phosphoric compounds, esterified products of the phosphoric compounds, alkali metal salts or ammonium salts of the phosphoric compounds, compounds obtained by introducing an ester linkage and an alkali metal salt linkage or an ammonium salt linkage into the phosphoric compounds, and hexaalkylphosphorus triamides.

15. The polymerization-inhibiting method according to claim 14, wherein the compound (a) is at least one compound selected from the group consisting of an N,N-dialkylhydroxylamine, a sterically hindered nitroxyl compound and a sterically hindered hydroxylamine compound.

16. The polymerization-inhibiting method according to claim 15, wherein the N,N-dialkylhydroxylamine is a compound represented by the formula (I):

(I)

wherein $R_1$ and $R_2$ are independently a linear, branched or cyclic alkyl group having 1 to 10 carbon atoms.

17. The polymerization-inhibiting method according to claim 15, wherein the sterically hindered nitroxyl compound is a compound represented by the formula (II):

(II)

wherein the nitrogen atom is bonded directly to 2 disubstituted carbon atoms, $E_1$, $E_2$, $E_3$ and $E_4$ are independently an organic group, and T is an organic group required to form a 5- or 6-membered ring, or a compound represented by the formula (IV):

(IV)

wherein the nitrogen atom is bonded directly to 2 disubstituted carbon atoms, $E_1$, $E_2$, $E_3$ and $E_4$ are independently an organic group, and X is a divalent linking group.

18. The polymerization-inhibiting method according to claim 15, wherein the sterically hindered hydroxylamine compound is a compound represented by the formula (III):

(III)

wherein the nitrogen atom is bonded directly to 2 disubstituted carbon atoms, $E_1$, $E_2$, $E_3$ and $E_4$ are independently an organic group, and T is an organic group required to form a 5- or 6-membered ring, or a compound represented by the formula (V):

(V)

wherein the nitrogen atom is bonded directly to 2 disubstituted carbon atoms, $E_1$, $E_2$, $E_3$ and $E_4$ are independently an organic group, and X is a divalent linking group.

19. The polymerization-inhibiting method according to claim 7, wherein the compound (a) is an N,N-dialkylhydroxylamine.

20. The polymerization-inhibiting method according to claim 19, wherein the N,N-dialkylhydroxylamine is a compound represented by the formula (I):

(I)

wherein $R_1$ and $R_2$ are independently a linear, branched or cyclic alkyl group having 1 to 10 carbon atoms.

21. The polymerization-inhibiting method according to claim 20, wherein the phosphorus-containing compound (b) is at least one selected from the group consisting of phosphoric compounds, esterified products of the phosphoric compounds, alkali metal salts or ammonium salts of the phosphoric compounds, compounds obtained by introducing an ester linkage and an alkali metal salt linkage or an ammonium salt linkage into the phosphoric compounds, phosphine compounds, and hexaalkylphosphorus triamides.

* * * * *